(12) United States Patent
Ott et al.

(10) Patent No.: US 11,525,710 B2
(45) Date of Patent: Dec. 13, 2022

(54) MULTI-SENSOR COMPONENT FOR BIOPROCESS CONTROL

(71) Applicant: SCHOTT AG, Mainz (DE)

(72) Inventors: Christian Ott, Ampfing (DE); Christoph Kolberg, Landshut (DE)

(73) Assignee: SCHOTT AG, Mainz (DE)

( * ) Notice: Subject to any disclaimer, the term of this patent is extended or adjusted under 35 U.S.C. 154(b) by 174 days.

(21) Appl. No.: 16/915,442

(22) Filed: Jun. 29, 2020

(65) Prior Publication Data

US 2020/0408575 A1 Dec. 31, 2020

(30) Foreign Application Priority Data

Jun. 27, 2019 (DE) .................... 10 2019 117 446.5

(51) Int. Cl.
| | |
|---|---|
| *G01D 5/26* | (2006.01) |
| *G01D 11/24* | (2006.01) |
| *C12M 1/00* | (2006.01) |
| *G01D 11/26* | (2006.01) |
| *C12M 1/24* | (2006.01) |
| *C12M 3/00* | (2006.01) |
| *C12M 1/34* | (2006.01) |

(52) U.S. Cl.
CPC .......... *G01D 11/245* (2013.01); *C12M 23/00* (2013.01); *C12M 23/08* (2013.01); *C12M 23/48* (2013.01); *C12M 41/06* (2013.01); *C12M 41/30* (2013.01); *G01D 5/268* (2013.01); *G01D 11/26* (2013.01)

(58) Field of Classification Search
None
See application file for complete search history.

(56) References Cited

U.S. PATENT DOCUMENTS

| 7,041,493 B2 * | 5/2006 | Rao .................. C12M 41/26 435/288.1 |
| 2002/0025547 A1 * | 2/2002 | Rao .................. C12M 41/32 435/40.5 |
| 2010/0035337 A1 * | 2/2010 | Bahnemann .......... C12M 41/36 435/292.1 |
| 2012/0097557 A1 * | 4/2012 | Baumfalk ............... C22B 19/30 206/216 |

(Continued)

FOREIGN PATENT DOCUMENTS

| CN | 201658978 | 12/2010 |
| CN | 202297585 | 7/2012 |

(Continued)

*Primary Examiner* — Lisa M Caputo
*Assistant Examiner* — Nigel H Plumb
(74) *Attorney, Agent, or Firm* — Ruggiero McAllister & McMahon LLC

(57) ABSTRACT

A multi-sensor component for the installation of at least two sensors at an individual port of a container for culturing biological material is provided. The multi-sensor component has a housing that can be introduced by a front housing segment into an uptake opening extending through the port of the container so that the front housing segment is facing the inside of the container. The multi-sensor component has a first sensor unit or a mount for a first sensor unit arranged on the front housing segment and has a second sensor unit or a mount for a second sensor unit arranged on the front housing segment.

17 Claims, 7 Drawing Sheets

(56) References Cited

U.S. PATENT DOCUMENTS

| | | | | |
|---|---|---|---|---|
| 2013/0039810 A1* | 2/2013 | Riechers | ............... | C12M 41/02 |
| | | | | 422/82.05 |
| 2015/0218501 A1* | 8/2015 | Kauling | ................. | C12M 29/20 |
| | | | | 435/325 |
| 2016/0305897 A1* | 10/2016 | Furey | .................. | G01D 11/245 |
| 2017/0219512 A1* | 8/2017 | Wunderlich | ....... | G01N 27/4161 |
| 2020/0071654 A1* | 3/2020 | Heo | ................... | B01F 25/4231 |

FOREIGN PATENT DOCUMENTS

| | | |
|---|---|---|
| DE | 19819857 | 11/1998 |
| DE | 202009010255 | 10/2009 |
| DE | 102009037345 | 12/2010 |
| DE | 102010007559 | 8/2011 |
| DE | 102013015106 | 3/2015 |
| DE | 202016000554 | 5/2017 |
| DE | 102016101715 | 8/2017 |
| EP | 2371942 | 10/2011 |
| EP | 3109314 | 12/2016 |
| JP | H06141850 | 5/1994 |
| JP | 2007202542 | 8/2007 |
| WO | 9008816 | 8/1990 |
| WO | 2014044612 | 3/2014 |
| WO | 2018037402 | 3/2018 |
| WO | 2018097510 | 5/2018 |

* cited by examiner

FIG. 6
FIG. 7
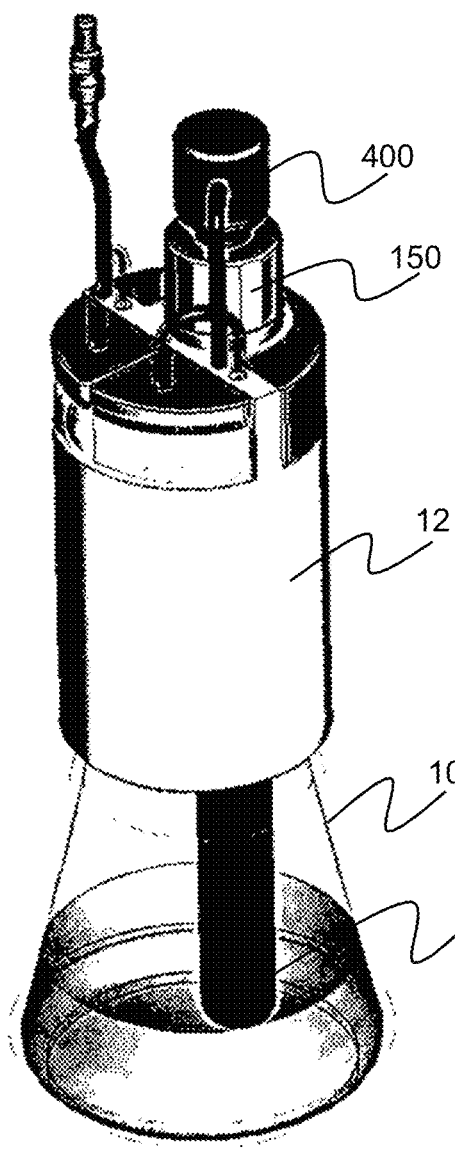
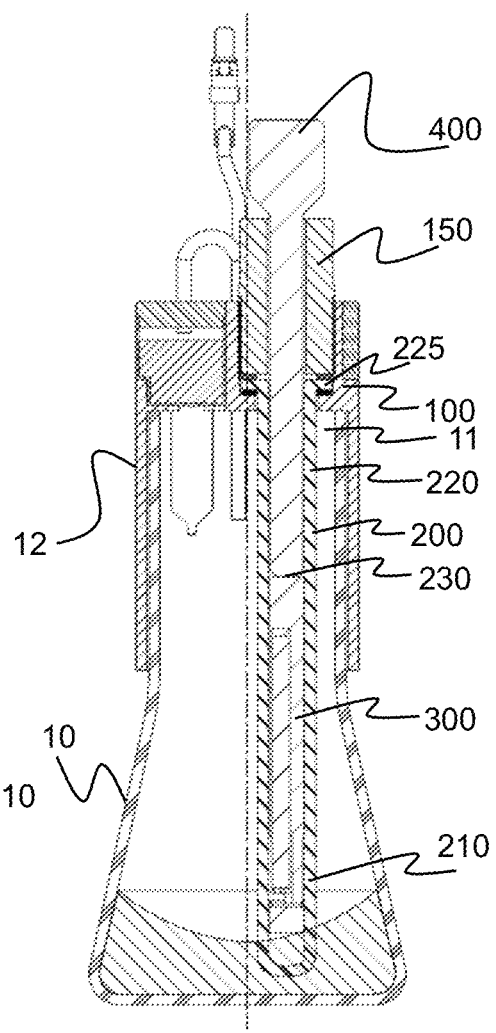

FIG. 8
FIG. 9
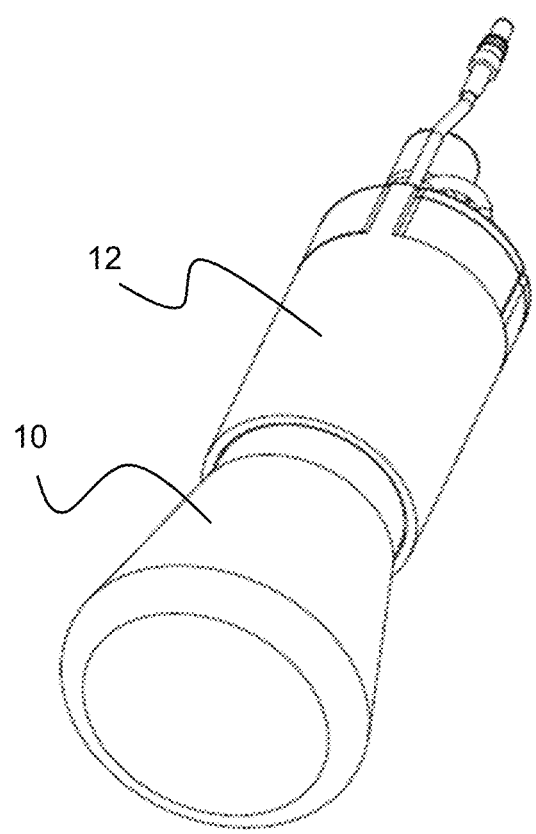
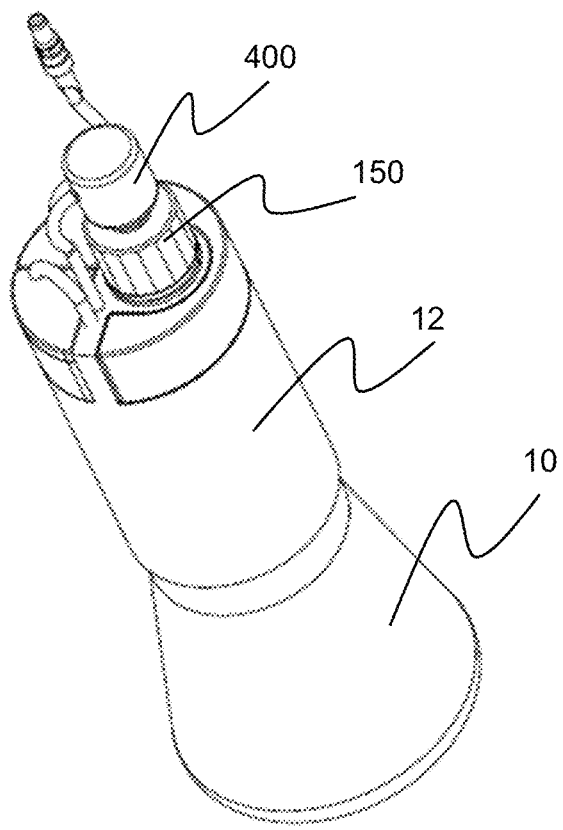

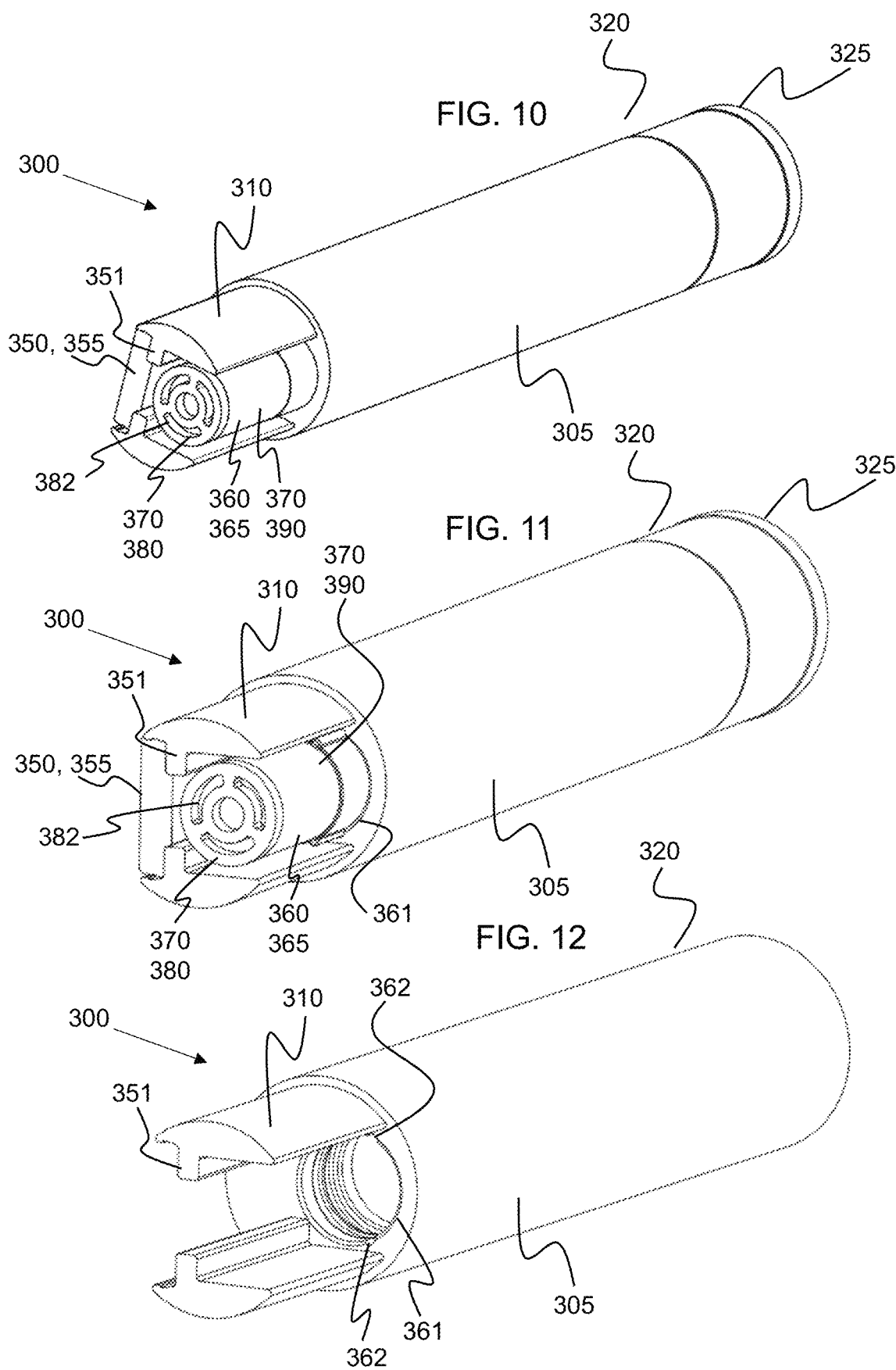

MULTI-SENSOR COMPONENT FOR BIOPROCESS CONTROL

CROSS REFERENCE TO RELATED APPLICATIONS

This application claims benefit under 35 USC § 119 of German Application No. 10 2019 117 446.5 filed Jun. 27, 2019, the entire contents of which are incorporated herein by reference.

BACKGROUND

1. Field of the Invention

The invention relates to process control in the case of production processors in containers for culturing biological material, in particular bioreactors and shake flasks.

2. Description of Related Art

Bioreactors and shake flasks are used for culturing microorganisms, animal and plant cells, and thus open up a broad field of application for biotech production processes. In general, there is a need for further optimizing these processes. In particular, for the production of biopharmaceuticals, improvements in product yield and thus increases in profit are targeted. Various approaches are provided for controlling and control of production processes, increasing product yield, as well as the reduction of costs.

On the one hand, a controlling and control of processes can be produced by determining the concentrations of the substrate and the product. This is time-consuming, of course, and usually requires resource-intensive offline analytics. Due to the drawing of samples, there is also a not insignificant risk of contamination.

On the other hand, the control of processes and thus the yield can be optimized by conducting a real-time process control of key parameters. In order to increase the product yield, in-situ monitoring of parameters, such as temperature, substances relevant to metabolism or to product formation, as well as a regulation of culturing conditions in real time are particularly advantageous.

Biosensors can be used for real-time parameter control. Such biosensors, in particular, can be installed at a port of a bioreactor, a shake flask, or, in general, any disposable or reusable container for culturing biological material, since such a port forms an opening into the inside of the container. The port of a bioreactor or shake flask frequently corresponds to a specific standard, thus, for example, an Ingold port or a Broadly-James port.

Sometimes it is also desired to monitor several key parameters. For this purpose, an additional biosensor can be installed at another port of the container. In addition, it may be desired to monitor parameters by means of spectroscopic methods, in which the quenching of luminophores is detected.

Of course, an increasing risk of contamination can be a disadvantage in the parallel monitoring of several parameters. In addition, the number of available ports may be limited, particularly in the case of smaller containers or in shake flasks.

SUMMARY

Accordingly, the object of the invention is based on making possible a real-time parameter control of several parameters with a reduction in the risk of contamination, and/or on monitoring several parameters even in containers with a small number of available ports.

According to the invention, a multi-sensor component is provided for the installation of at least two sensors at an individual port of a container for culturing biological material, in particular a bioreactor or shake flask.

The multi-sensor component according to the invention comprises a housing that can be introduced at least by a front housing segment into an uptake opening extending through the port of the container, so that the front housing segment is facing the inside of the container.

The uptake opening extending through the port of the container can be formed, for example, by the port itself, i.e., it can be the passage opening, which is formed by the port in the container wall and which connects the inside of the container to the outside of the container. In other words, the multi-sensor component according to the invention can be introduced directly into the port.

In a preferred embodiment, however, it is provided that the uptake opening extending through the port of the container involves an opening within an intermediate element that can be introduced into the port, in particular a sensor uptake, such as will be described in more detail below. In this case, the multi-sensor component according to the invention can be introduced, for example, directly into the intermediate piece or the sensor uptake and thus indirectly into the port.

In a preferred embodiment, the housing of the multi-sensor component is designed such that it can be introduced completely into an uptake opening extending through the port of the container, i.e., it is completely surrounded, particularly radially, by the port or a sensor uptake. The housing of the multi-sensor component accordingly may particularly have a uniform outer form along the longitudinal axis of the multi-sensor component; thus, in particular, it can be formed cylindrically, particularly along the entire length of the multi-sensor component.

The housing of the multi-sensor component according to the invention has in its front housing segment either a first sensor unit or at least a mount for a first sensor unit. In addition, a second sensor unit or at least a mount for a second sensor unit is arranged in the front housing segment.

A sensor unit is accordingly preferably arranged in the front housing segment, thus facing the inside of the container, and, in particular is found inside the container when the multi-sensor component is introduced into the uptake opening extending through the port of the container. Further, a mount for a sensor unit is preferably arranged in the front housing segment, thus facing the inside of the container, and, in particular is found inside the container when the multi-sensor component is introduced into the uptake opening extending through the port of the container. In addition, a mount for a sensor unit is preferably equipped to mount a sensor unit, so that it faces the inside of the container, and, in particular is found inside the container when the multi-sensor component is introduced into the uptake opening extending through the port of the container.

For example, two, in particular different, sensor units can be arranged accordingly in the front housing segment. It may also be provided, however, that a first sensor unit and a mount for a second, in particular different, sensor unit are arranged in the front housing segment. Also, two mounts may be provided, namely a mount for a first sensor unit as well as a mount for a second, in particular different, sensor unit. Of course, still more sensor units and/or mounts for sensor units may also be present.

With the multi-sensor component, which comprises at least two sensor units or mounts for sensor units, two or more sensors can be combined in one port in an advantageous way, which is of advantage in case available ports are limited, e.g., in the case of shake flasks. This makes possible, in particular, the need-oriented use of non-sterilizable sensors, combined in one port. In general, the invention relates to both multiple-use applications (glass or stainless-steel bioreactors), single-use applications (so-called disposable bioreactors or bags), but also shake incubators (shake flasks and cell culture flasks).

Preferably, at least one sensor unit is designed as a biosensor unit, in particular for analyte-specific parameter measurement. In other words, the sensor unit, the sensor units, or one of the sensor units can be designed as a biosensor unit. A biosensor unit preferably comprises a bioreceptor, and is particularly equipped for the purpose of converting a biological signal into a physicochemical signal by way of the bioreceptor. For example, a biosensor unit can be designed for the purpose of determining a concentration of saccharides or proteins.

In the case where one or two mounts are provided for a first and/or a second sensor unit, alternatively at least one of the mounts is designed for mounting a biosensor unit as described above. Of course, both mounts may also be designed correspondingly. In addition, the two can also optionally be provided successively, for example, the first sensor unit is designed as a biosensor unit as described above, and the mount for the second sensor unit is designed for mounting a sensor unit designed as a biosensor unit as described above.

A biosensor unit can be designed as a preferably modular structural unit, for example, in the form of a flat chip, and/or it may be provided that a corresponding mount is designed for mounting such a structural unit.

Further, at least one sensor unit, particularly a sensor unit that is not designed as a biosensor unit, is preferably designed as a luminophore unit for luminescence-based parameter measurement. In other words, the sensor unit, the sensor units, or one of the sensor units can be designed as a luminophore unit.

In the case where one or two mounts are provided for a first and/or a second sensor unit, alternatively at least one of the mounts is designed for mounting a luminophore unit as described above. Of course, both mounts may also be designed correspondingly. In addition, the two can also optionally be provided successively; for example, the first sensor unit is designed as a luminophore unit as described above, and the mount for the second sensor unit is designed for mounting a sensor unit designed as a luminophore unit as described above.

Particularly preferred, it may be provided that the first sensor unit is designed as a biosensor unit or the corresponding mount is designed for mounting a biosensor unit, and the second sensor unit is designed as a luminophore unit or the corresponding mount is designed for mounting a luminophore unit.

In other words, the invention makes possible, in particular, the combined use of luminophores and biosensors, in which a luminophore unit and a biosensor unit are integrated in one housing. The invention thus relates to a "multi-sensor unit", e.g., for the production of biopharmaceuticals. The evaluation of multiple parameters is thereby made possible by measurement in one port (via luminophores and biosensors).

A sensor unit can also be designed as an alternating field unit for dielectricity-based parameter measurement. In addition, a sensor unit can also be designed as a transistor unit for parameter measurement based on field effects. Moreover, a mount for one of the above sensor units can also be provided.

A sensor unit or a corresponding mount can have at least one dimension running perpendicular to the longitudinal direction of the multi-sensor component that is greater than 35%, preferably 50%, particularly preferred 65% of the thickness of the multi-sensor component perpendicular to the longitudinal direction thereof. Preferably, a biosensor unit or a mount for a biosensor unit can have such a dimension. Further, preferably, a luminophore unit or a mount for a luminophore unit can have such a dimension. Also, an alternating field unit or a transistor unit or a mount for such a unit can have such a dimension.

An analyte-specific parameter measurement with a biosensor unit can imply that a certain measurement variable, the analyte, is detected selectively, in particular that not several parameters are detected at the same time, e.g. different analytes are detected at the same time.

With luminescence-based parameter measurement with a luminophore unit, analyte-dependent signal quenching can take place. Through interaction with the measurement variable, the excitation wavelength can be shifted in wavelength and/or phase.

If charges move in the electric field in analytes, a dipole is induced. In the case of a dielectricity-based measurement with an alternating field unit, a frequency-dependent interaction in the sensor unit can be used.

In the case of a field effect-based parameter measurement with a transistor unit, ionic analytes can induce a conductivity-producing mirror charge at a semiconductor element, in particular by reversibly attaching themselves ion-selectively to a sensor chip.

A sensor unit designed as a luminophore unit preferably comprises a basic body with an uptake means for accommodating a luminophore substance, whereby the uptake means is particularly designed as a cavity in the basic body. Of course, in the case of one or two mounts, it may be provided in turn that a corresponding mount is designed for mounting such a basic body.

The basic body of a luminophore unit may have a front region and a back region, such that the front region of the basic body is facing the inside of the container, and the back region of the basic body is facing the outside of the container, when the luminophore unit is introduced into the port or the uptake opening extending through the port of the container, and/or when the multi-sensor component or the front housing segment thereof is introduced into the port or the uptake opening extending through the port of the container.

In this case, the front region of the basic body comprises the at least one uptake means that is particularly designed as a cavity. Alternatively or additionally, the back region of the basic body can comprise at least one light guide and preferably one light source (laser, LED, VCSELs (Vertical-Cavity Surface-Emitting Lasers)) in order to guide light of a light source to the uptake means and/or to guide light from the uptake means to a photodiode.

The front region of the basic body can comprise material comprising glass, in particular glass or glass ceramics, or be composed of such material, whereby the uptake means are introduced as cavities in the material by means of laser cutting.

The back region of the basic body can comprise optical fibers or be composed thereof, whereby the fibers preferably form, at least partially, the already mentioned light guide, in order to guide light to the uptake means preferably designed as a cavity.

In a preferred embodiment, the front region of the basic body, which particularly comprises glass, is designed as a plate or disc, and/or the back region of the basic body, preferably comprising optical fibers, is designed in rod shape. Further, the front region of the basic body can be joined to the back region of the basic body by laser welding.

The basic structure of the luminophore unit can therefore be a fiber rod, wherein the latter may be provided on the end that has cavities and that faces the medium or contacts the medium. As described, such cavities can be produced by cutting out corresponding segments from a glass plate or disc using a laser, and subsequently producing a material bond with the fiber rod by way of laser welding.

The glass fibers of the fiber rod aligned on a particular luminophore cavity can be excited by LED or laser light. Depending on the analyte concentration, the rate of the quenching of the excited states can be guided via the corresponding glass fibers from the luminophore to the detector cells, wherein, for example, photodiodes integrated in the housing can be provided. Space limitations can be compensated for during the coupling and decoupling of light by the use of one or more light guides.

Basically, the luminophore unit is equipped for the purpose of taking up or accommodating luminophore substance. In another embodiment, this substance may already be contained therein, however. Accordingly, it can be provided that the luminophore unit comprises a luminophore substance, wherein the substance is preferably accommodated by an uptake means of the basic body that is designed as a cavity. The substance can be fixed in place thermally to or in the uptake means, e.g., the cavity.

The uptake means or cavities can be designed for the purpose of accommodating a liquid or gel-type luminophore substance, or can already comprise such a substance. The luminophore substance can accordingly be designed particularly as a soft mass (i.e., in particular softer than the basic body and/or the front region of the basic body). In the case of several cavities, in particular, the luminophore can be individually introduced into the cavities. This makes possible a combination of optimal parameters for a process control (pH, $pO_2$, $pCO_2$, temperature, conc. saccharides, proteins, etc., wherein saccharides and proteins can preferably be determined with the biosensor unit) in the selected measurement region in a port of a bioreactor, shake flask or other container having a port.

Accordingly, several uptake means can be provided in the basic body or front region of the basic body, wherein each of these can be designed as a cavity, so that advantageously, several, in particular different, luminophore substances can be used.

The luminophore substance or the luminophore comprises, in particular, graphene quantum dots (GQDs), heterocyclic GQDs (e.g., N-GQDs) and/or an organometallic compound. The following are particularly considered: DHFAE: 2,7'-dihexyl-5(6)-noctadecyl-carboxamidofluorescein ethyl ester and the phosphorescent ruthenium(II)-tris-4,7-diphenyl-1,10-phenanthroline as inert reference standard; pH-sensitive fluorescent dye for the pH region 7.3-9.3; HPTS: 8-hydroxypyrene-1,3,6-trisulfonic acid as a trisodium salt; pH-sensitive fluorescent dye for the pH region 5.5-8.6 (Zhu et al. 2005); PtOEP: platinum "12,13,17,18-octaethyl-21H,23H-porphyrin pH-sensitive fluorescent dye; Pt-PFP: platinum(II) meso-tetra(pentafluorophenyl)porphyrin $O_2$-sensitive fluorescent dye for the region $0\% > O_2 > 21\%$; ruthenium(II) diimine complex: ruthenium(II) tris-4,7-diphenyl-1,10-phenanthroline, with trimethylsilyl propanesulfonate as counter-ion; and $O_2$-sensitive fluorescent dye for the region $0\% > O_2 > 21\%$ A xerogel can be produced from or with an organometallic compound, in particular one of the above-named compounds having organically modified silicate. Depending on the application, ultrafine ground glass powder or dual-core CoralPor® particles can be added to the mixture for the matrix. The porous structure can be used for the distribution of the organometallic substances in the sol-gel matrix. The concentrating in the pores can form a criterion in order to improve the sensor sensitivity and response time. Such a mix is a luminophore or a luminophore substance and can be accommodated by an uptake means, in particular a cavity, in the basic body. For example, the luminophores for $pO_2$, $pCO_2$, pH, temperature, etc. can each be introduced into a corresponding cavity and can be thermally fixed in place therein.

In addition to the above-named organometallic compounds, the luminophore substance therefore further can also comprise ground glass powder. In particular, this substance can be produced or is producible by means of a sol-gel method and, e.g., can be used as a xerogel.

The multi-sensor component can be designed so that at least one sensor unit can be fastened to the front housing segment by sliding it in, clipping it in, and/or snapping it in, and/or so that at least one mount is designed for sliding, clipping, and/or snapping in a sensor unit. Further, a mount can be designed for contacting the sensor unit.

In particular, the biosensors selected for the particular culturing, roughly in the form of a biosensor chip, can thus be clipped in or can be contacted in a guide on the housing.

Overall, the described multi-sensor component thus represents a universal and variously adaptable system. This unique sensor concept makes possible the realization of various systems, for example, a system based on a described multi-sensor component and via combination with different organometallic compounds, and/or biosensor chips.

The structural shape is basically designed for universal usability for any type of uptake opening. Preferably, the structural shape can be designed for standardized ports (standard connections) of classical bioreactors, for ports of disposable or single-use bioreactors or bags or also for shake flask applications.

Preferred use finds the multi-sensor unit together with the maintaining of requirements for sterile culturing conditions. Accordingly, in a preferred embodiment, it is provided that a sensor uptake extending through the port of the container forms the uptake opening for the multi-sensor component. Such a sensor uptake is equipped particularly for the purpose of maintaining a sterility boundary between culturing space and sensor. Further, for maintaining sterile culturing conditions, it is provided that the multi-sensor component is or will be aseptically pretreated prior to its sterilely reliable accommodation in an uptake opening.

The invention further relates to a system for the installation of at least two sensors at an individual port of a container for culturing biological material, in particular a bioreactor or a shake flask, wherein the system comprises a sensor uptake and a multi-sensor component as described above.

The sensor uptake has an inner uptake opening, wherein the sensor uptake can be introduced at least by a front sensor uptake section into the port of the container, so that the inner uptake opening of the sensor uptake extends through the port of the container.

The multi-sensor component has a housing that can be introduced at least by a front housing segment into the uptake opening of the sensor uptake extending through the port of the container, so that the front housing segment is facing the inside of the container.

In a preferred embodiment, the housing of the multi-sensor component is designed such that it can be introduced completely into an uptake opening extending through the port of the container, i.e., it is surrounded completely, particularly radially, by the sensor uptake in the installed state. The housing of the multi-sensor component accordingly may have a uniform outer form along the longitudinal axis of the multi-sensor component, thus, in particular, it can be formed cylindrically, particularly along the entire length of the multi-sensor component.

The inner uptake opening of the sensor uptake is open in particular to the outside of the container, so that the multi-sensor component can be introduced particularly from the outside into the uptake opening. Preferably, the inner uptake opening has a uniform cross section along its longitudinal direction; thus, it is particularly designed cylindrically, in particular over a portion of the longitudinal direction comprising the end section of the uptake opening that is open to the outside.

It can be provided in the system that the sensor uptake is designed closed in the front sensor uptake section, so that the inner uptake opening of the sensor uptake is open to the outside of the container and is closed to the inside of the container, when the sensor uptake is introduced into the port.

The front sensor uptake section can have an open porosity, at least in regions. The pore size can amount to, e.g., between 40 and 300 nanometers.

In addition, the invention also relates to a container for culturing biological material, in particular a bioreactor or a shake flask, comprising a port, which connects the inside of the container to the outside of the container in typical manner, as well as a multi-sensor component and—optionally—also a sensor uptake.

The sensor uptake has an inner uptake opening, wherein the sensor uptake is introduced at least by a front sensor uptake section into the port of the container, so that the inner uptake opening of the sensor uptake extends through the port of the container. A multi-sensor component having a housing is introduced at least by a front housing segment into the uptake opening of the sensor uptake extending through the port of the container, so that the front housing segment is facing the inside of the container.

In the case when a sensor uptake is not provided, the port that connects the inside of the container with the outside of the container forms the uptake opening extending through the port. The multi-sensor component having a housing is then introduced at least by a front housing segment into the uptake opening extending through the port of the container, so that the front housing segment is facing the inside of the container.

The invention further relates to a luminophore unit for luminescence-based parameter measurement, in particular for installing in a multi-sensor component having a mount for mounting a luminophore unit, as it has been described above, for example. For details and/or further embodiments of the luminophore unit, the above statements apply correspondingly.

In addition, the invention also relates to a method for producing a multi-sensor component, as it has been described above, for example.

According to a variant of the method, first a sensor unit can be provided, in particular a luminophore unit, for example, as described above, as well as a housing, wherein the provided housing can be introduced at least by a front housing segment into an uptake opening extending through the port of a container, so that the front housing segment is facing the inside of the container, wherein the provided housing further has a recess for a sensor unit, in particular a luminophore unit, on the front housing segment, and wherein the housing preferably comprises a polymer material, in particular polyether ether ketone (PEEK), or is composed of such a material.

In a further method step, a relative expansion of the housing opposite the sensor unit can then be brought about, in particular, by heating the housing. Then the sensor unit can be installed in the expanded recess of the housing, which is expanded opposite the sensor unit. The housing solidly accommodates the sensor unit in the recess in this way; then, in turn, a relative contraction of the housing can be brought about opposite the sensor unit by cooling the housing.

According to another variant of the method, first a sensor unit can be provided, in particular a luminophore unit, for example, as described above, as well as a liquid polymer, for formation of a housing, wherein the liquid polymer that is provided particularly comprises polyethylene or polypropylene or is composed thereof.

In further method steps, the liquid polymer can then be supplied to the sensor unit from the outside and can be caused to harden in such a way that a housing that solidly accommodates the sensor unit is formed.

BRIEF DESCRIPTION OF THE DRAWINGS

Several special non-limiting embodiment examples for understanding the invention, with reference to the appended drawings, are explained below.

FIG. 6 is a three-dimensional view of a shake flask with a shake flask cap having a port;

FIG. 7 is a sectional view of a shake flask with a shake flask cap having a port and a sensor uptake, wherein an installed multi-sensor component can be seen in this sectional view;

FIGS. 8-9 are additional three-dimensional views of a shake flask with a shake flask cap having a port and a sensor uptake;

FIG. 10 is a three-dimensional view onto the front housing segment of a multi-sensor component having a biosensor unit and a luminophore unit, wherein the luminophore unit is solidly accommodated in the housing;

FIG. 11 is a three-dimensional view onto the front housing segment of a multi-sensor component having a biosensor unit and a luminophore unit, wherein the luminophore unit is fastened in an exchangeable manner in a corresponding mount in the housing;

FIG. 12 is a three-dimensional view onto the front housing segment of a multi-sensor component having a mount for a biosensor unit and a mount for a luminophore unit;

DETAILED DESCRIPTION

FIGS. 1-5 show different views of a port 100 in a wall 20 of a bioreactor, wherein the wall 20 of the bioreactor—which is shown here only in regions—bounds the inside of the bioreactor from the outside thereof. In the example shown there, the bioreactor involves a multi-use bioreactor, for example, manufactured of stainless steel, for multiple applications. Likewise, however, a single-use bioreactor, which is made of plastic, for example, for single-use applications, or in general any other container having a port 100 can be used.

In the example shown here, the port 100, which is found in the wall 20 of the bioreactor and which provides a passage through the wall 20 is designed as an Ingold port or an Ingold connection piece. Basically, however, any type of port 100 that forms an opening through the wall 20 is considered. Other standard ports are, for example, Broadly-James ports or B. Braun safety ports.

The wall 20 of the bioreactor has an inner side 22 facing the inside as well as an outer side 24 facing the outside. The inner side 22 of the wall 20 is facing the inner side of the bioreactor and is to be allocated to the sterile region, while the outer side 24 of the wall 20 of the bioreactor is facing the outside and is to be allocated to the non-sterile region.

Figure 1:
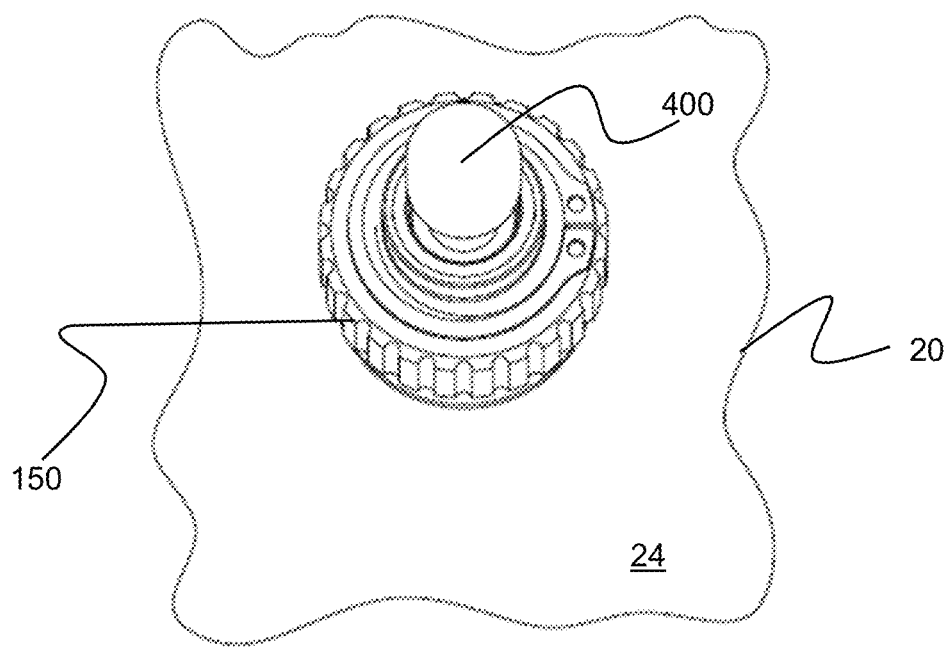
FIG. 1 is a three-dimensional view of a port of a bioreactor with sensor uptake.
Figure 2:
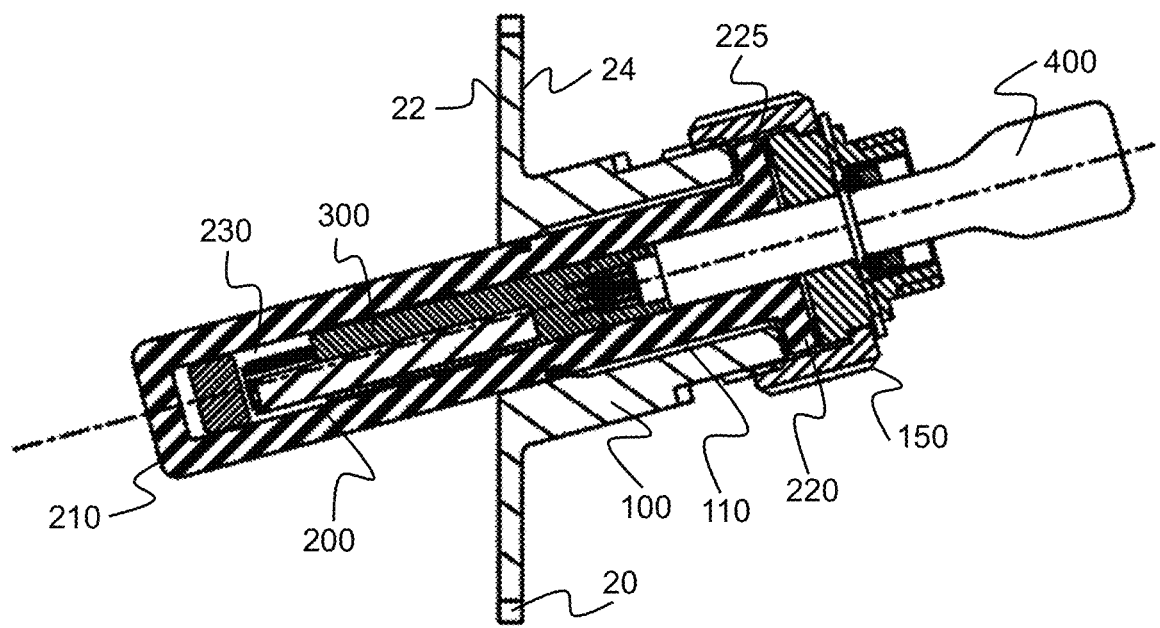
FIG. 2 is a sectional view of a port of a bioreactor with sensor uptake, wherein an illustration of an installed multi-sensor component can be seen in this sectional view.
Figure 3:
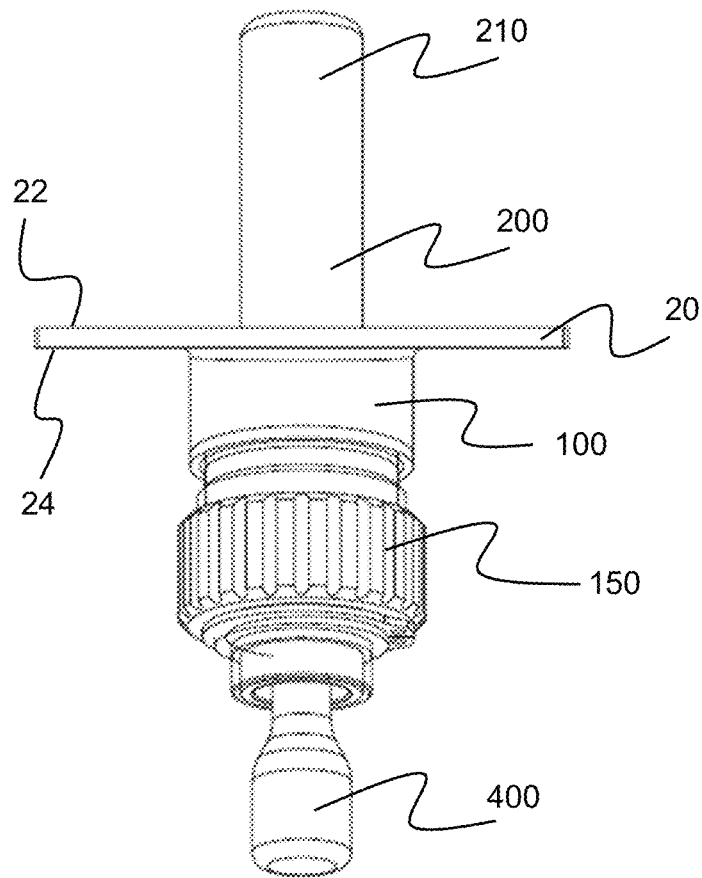
FIGS. 3-5 are additional three-dimensional views of a port of a bioreactor with sensor uptake.
Figure 4:
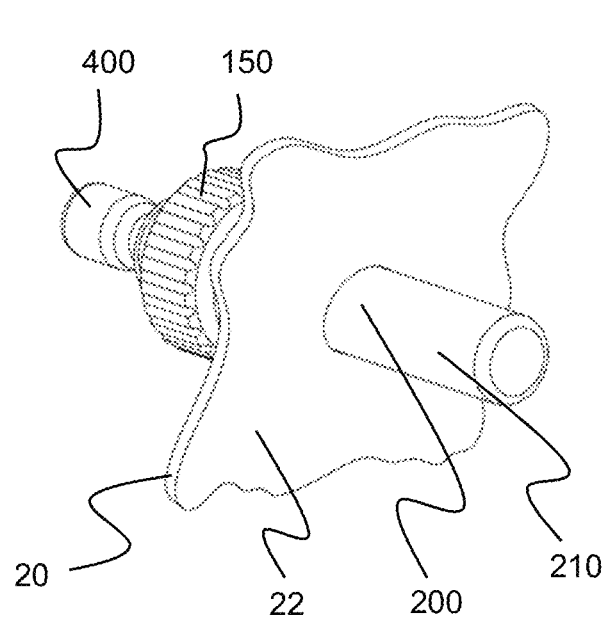
Figure 5:
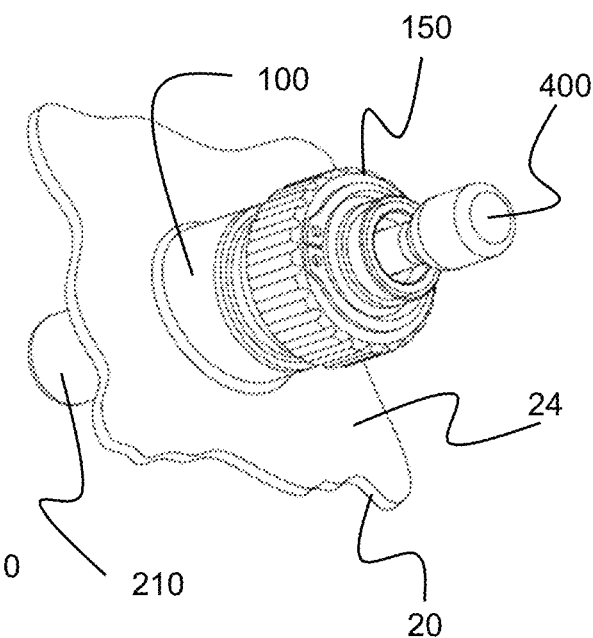

As can be best seen in FIG. 2, a sensor uptake 200 is accommodated inside the port 100, which also simultaneously forms an uptake opening 110 by its passage opening into the inside of the container. The sensor uptake 200 extends at least partially through the passage opening in the wall 20 formed by the port 100 and is mounted in the port 100. In the example shown, the sensor uptake 200 also is locked or can be locked detachably in the port 100 by a cap nut 150. The sensor uptake 200 projects by a front sensor uptake section 210 into the inside of the container and in this exemplary embodiment, also projects by a back sensor uptake section 220, on which a flange 225 is found, to the outside of the container.

The sensor uptake 200 comprises an inner uptake opening 230, which, in the example shown, is open to the back sensor uptake section 220 directed toward the outside. It may be provided, as shown, that the uptake opening 230 is closed toward the front sensor uptake section 210 directed toward the inside. The sensor uptake 200 is thus also designated the "sterile port". The front sensor uptake section 210 can have an open porosity, at least in regions.

FIGS. 6-9 show different views of a shake flask 10 having a shake flask cap 12. The shake flask cap 12 seals the opening 11 of the shake flask 10 and comprises a port 100 into the inside of the shake flask 10. Port 100 in turn can involve any type of passage opening, in particular a standardized port.

As can be best seen in FIG. 7, a sensor uptake 200 is accommodated in turn inside the port 100, which also simultaneously forms an uptake opening 110 by its passage opening into the inside of the container. The sensor uptake 200 extends at least partially through the port 100 and is mounted therein. In the example shown, the sensor uptake 200 is locked or can be locked detachably in the port 100 by means of a locking element 150. The sensor uptake 200 comprises in turn an inner uptake opening 230, which is open to the back sensor uptake section 220 and is closed to the front sensor uptake section 210.

Referring to FIG. 2 and FIG. 7, a multi-sensor component 300 is found in each case inside the uptake opening 230 of the sensor uptake 200. In the cases illustrated, the multi-sensor component 300 is installed completely in the uptake opening 230 of the sensor uptake and is detachably joined to a sensor head 400, in order to introduce the multi-sensor component 300 into the uptake opening 230 and to be able to remove it again. An electrical and/or optical connection can also exist between the sensor head 400 and the multi-sensor component 300, so that corresponding electrical and/or optical signals can be transmitted.

FIGS. 10-14 show in detail different embodiments of the multi-sensor component 300. In each case, the embodiments of the multi-sensor component 300 comprise a housing 305 with front housing segment 310, which can be seen best in FIGS. 10 to 12, and with back housing segment 320, which can be seen best in FIGS. 13 and 14.

On the first housing segment 310 are arranged a first sensor unit 350 and a second sensor unit 360, so that with the multi-sensor component 300, at least two sensors can be installed on a single port of a container for culturing biological material. The diameter of the housing 305 of the multi-sensor component 300 is dimensioned so that the multi-sensor component 300 can be introduced completely into an uptake opening 230 of a sensor uptake 200.

In the example shown in FIG. 10, one of the sensor units, here the first sensor unit 350, is designed as a modular biosensor unit 355, which can be introduced into a corresponding mount 351 on the front housing segment 310. At the same time or independently therefrom, one of the sensor units can be designed as a luminophore unit. Here, the second sensor unit 360 is designed as luminophore unit 365, which is fixed in place on the front housing segment 310, roughly by solidly taking it up in a recess in the front housing segment 310. For this purpose, in particular, a housing 305 comprising or composed of polyether ether ketone (PEEK) can be provided, which is produced by injection molding or also by an additive manufacturing method, and the housing is shrunk onto the luminophore unit 365; thus it was applied particularly for expansion and contraction, in order to fix in place the luminophore unit 365. On the other hand, a housing 305 with solidly accommodated luminophore unit 365 can also be produced by over-molding the housing material around the luminophore unit.

In the example shown in FIG. 11, in turn, one of the sensor units, here the first sensor unit 350, is designed as biosensor unit 355 mounted in a mount 351. At the same time or independently therefrom, in turn, one of the sensor units, here specifically the second sensor unit 360, can be designed as a luminophore unit 365. Distinguished from the example shown in FIG. 10, the luminophore unit 365 in this example is mounted in a mount 361 on the front housing segment 310. The luminophore unit 365 is accordingly mounted particularly as an exchangeable unit in the housing 305 or the mount 361.

The exemplary embodiment shown in FIG. 12 comprises a multi-sensor component 300—as does also the example shown in FIG. 11—a housing 305 having a front housing segment 310 and a back housing segment 320, wherein a first mount 351 for a first sensor unit 350 as well as a second mount 361 for a second sensor unit 360 are arranged in the front housing segment 310. In this case, the first mount 351 is designed again for mounting the biosensor unit 355. In addition, the second mount 361 can be designed for mounting a luminophore unit 365. Distinguished from the example shown in FIG. 11, the multi-sensor component 300 itself here does not comprise any sensor units.

Figure 13:
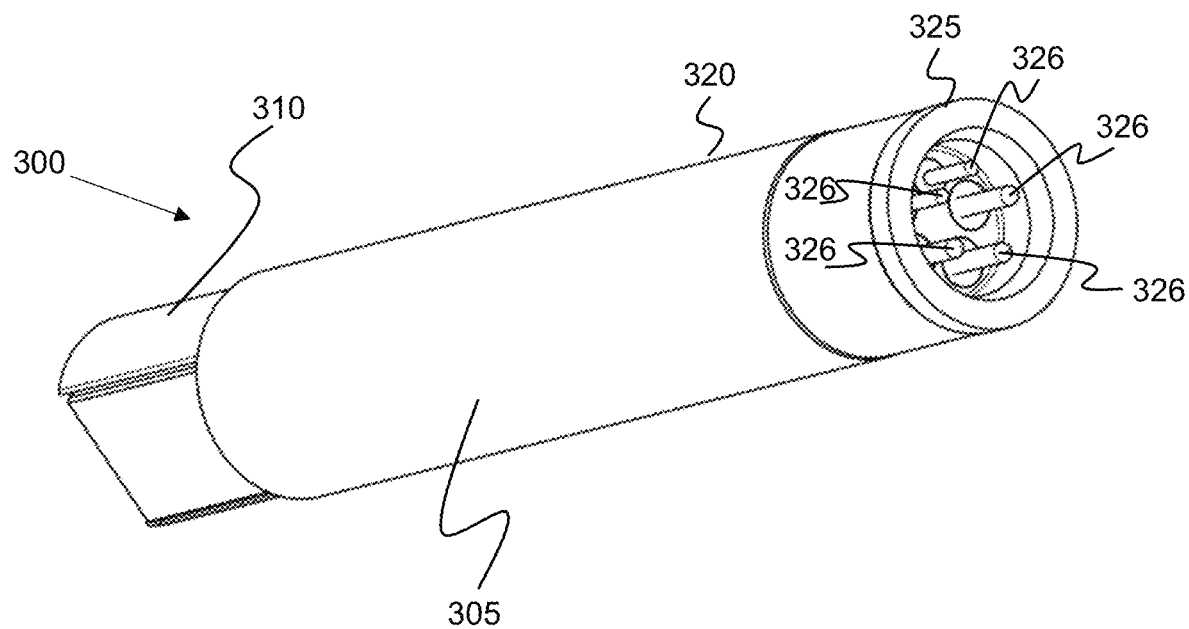
FIG. 13 is a three-dimensional view onto the back housing segment of a multi-sensor component with integrated light source and integrated photodiode.
Figure 14:
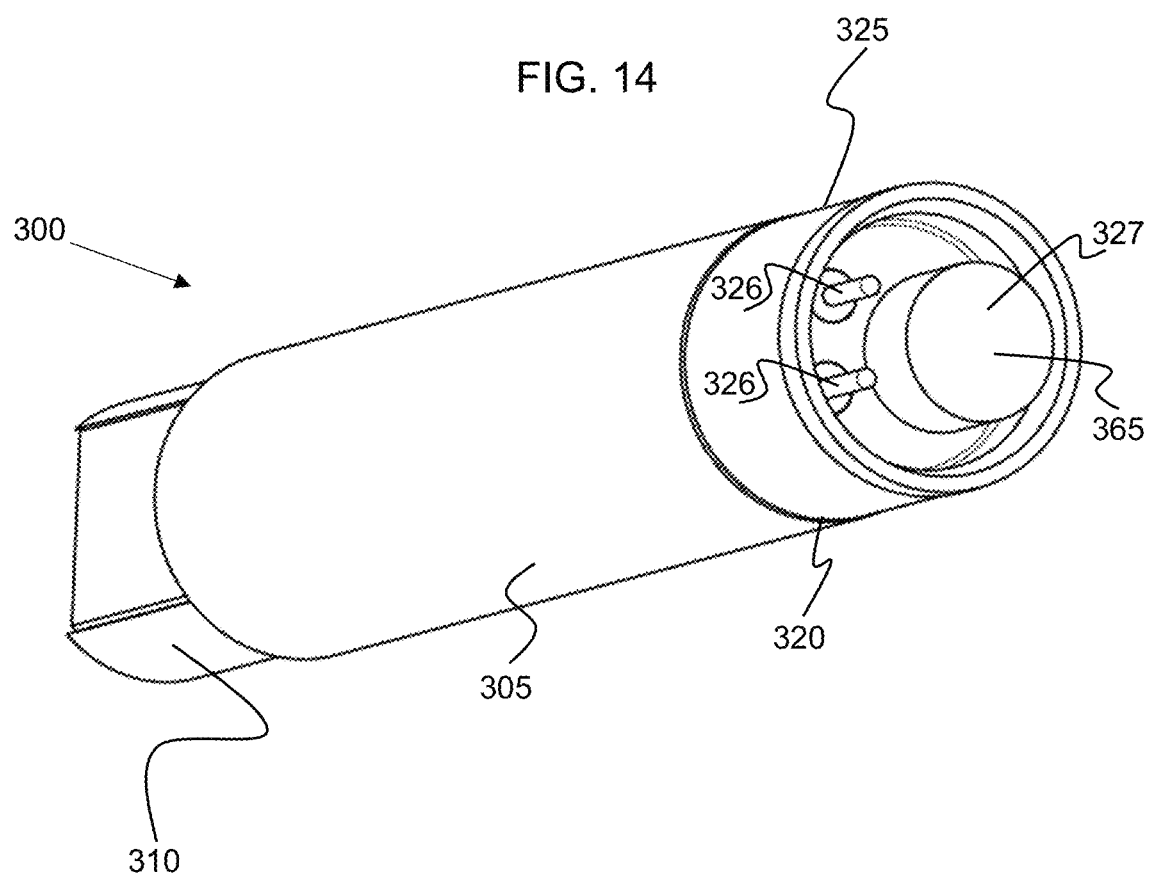
FIG. 14 is a three-dimensional view onto the back housing segment of a multi-sensor component, wherein the back region of the basic body of the luminophore unit is accessible, in order to interact with a light source and/or a photodiode.

The back housing segment 320 of a multi-sensor component 300, which can be best seen in FIGS. 13 and 14, can be executed differently, independently from the configuration of the front housing segment 310. Preferably, a connector 325 having electrical contact elements 326 and/or at least one optical contact element 327 is found in the back housing segment 320, in order to produce an electrical and/or optical connection to the multi-sensor component and preferably sensor units mounted or fastened therein.

The connector 325 of the multi-sensor component 300 can be designed in particular for the purpose of being joined to a sensor head 400 (in this regard, see, e.g., FIG. 2 and FIG. 7). Electrical contact elements 326, which can be designed as contact pins, are particularly provided for connection to a biosensor unit 355 or to a mount 351 for mounting a biosensor unit 355. On the other hand, electrical contact elements 326 may be designed, however, also for connection to a light source arranged in the housing 305 and/or to a photoelement arranged in the housing, e.g., a photodiode. The multi-sensor component 300 does not necessarily need to comprise a light source or a photoelement for the operation of the luminophore unit 365; rather, these components can also be found outside the multi-sensor component 300. In this case, one or more optical contact elements 327 can be provided, wherein here it particularly involves a light guide. In a preferred embodiment, the luminophore unit 365 has a light guide that is particularly designed in rod shape as a fiber rod, which opens up into the connector 325, as can be seen in FIG. 14.

Figure 15:
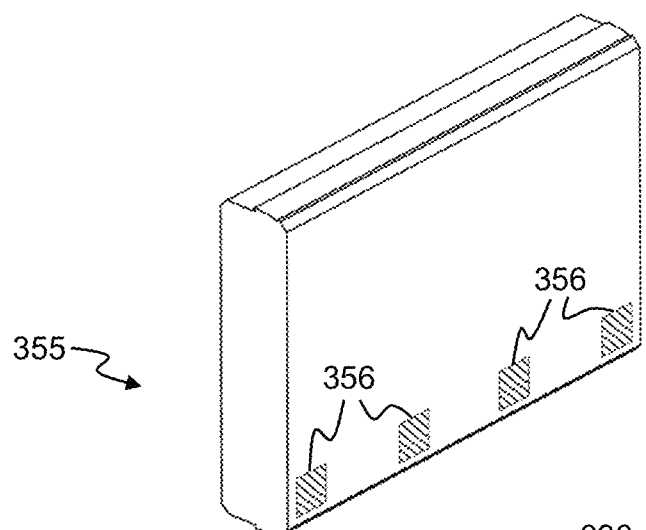
FIG. 15 is a three-dimensional view of a biosensor unit.
Figure 16:
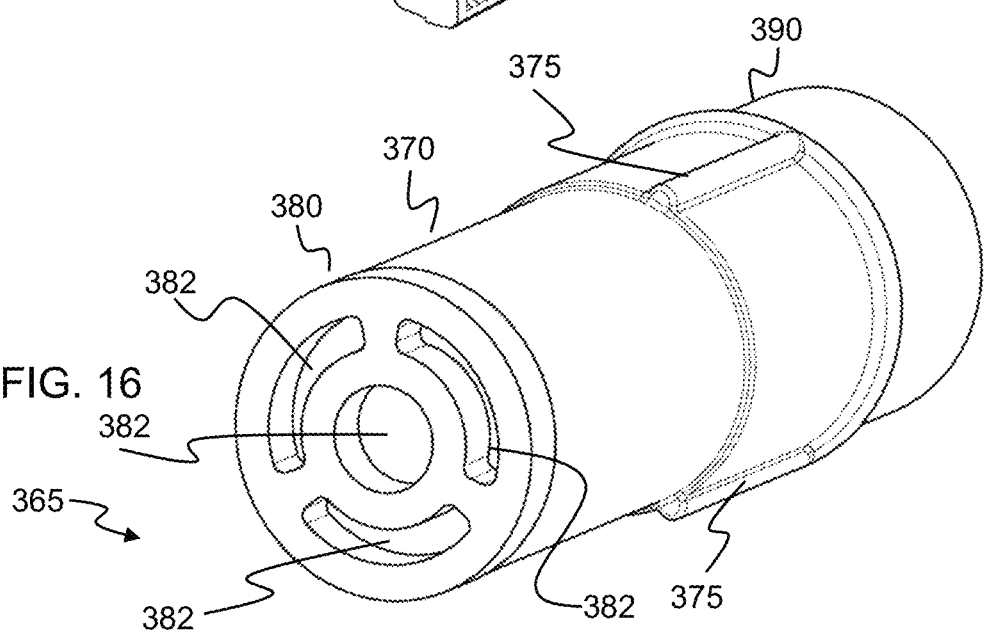
FIG. 16 is a three-dimensional view of a luminophore unit with front and back regions of the basic body.
Figure 17:
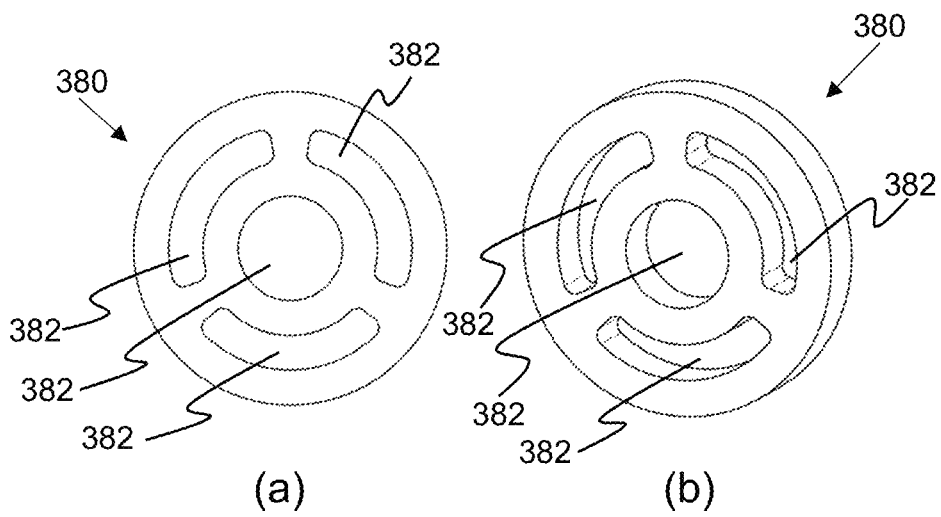
FIG. 17 is a top view (a) and a three-dimensional view (b) of the front region of the basic body of the luminophore unit from FIG. 16.

Referring to FIGS. 15-17, the sensor units, particularly the biosensor unit 355 and the luminophore unit 365, will be described below in more detail. Although an exchangeable luminophore unit 365 is shown in FIG. 16, the statements apply likewise to a solidly joined luminophore unit 365, as the latter can be seen roughly in FIG. 10.

The biosensor unit 355 shown in FIG. 15 has the form of a flat structural unit, whereupon other structural shapes can also be considered. The biosensor unit 355 is, of course, preferably shaped such that it can be introduced into a mount 351 provided therefor and can then be removed again from it. The biosensor unit preferably has contact elements 356, which can be designed as contact surfaces that are contacted in the mount 351.

The luminophore unit 365, which is shown in FIG. 16, comprises a basic body 370 with a front basic body region 380 and a back basic body region 390. The front basic body region 380, which is shown once more in detail in FIG. 17, is designed as a glass disc, in which several cavities 382 are introduced by means of laser processing for accommodating luminophore substance. The back basic body region 390 is designed as a glass fiber rod, so that, on the one hand, light from a light source can be guided to the cavities 382, and, on the other hand, luminescent light from the cavities in turn can be guided to a photoelement, e.g., a photodiode. The glass fiber rod can be joined to the glass disc comprising the cavities 382 by means of laser welding. In the case of an exchangeable luminophore unit 365, the latter may have a guide element 375 that is designed, e.g., as a guide crosspiece, which cooperates with a complementary guide element 362, which is designed, e.g., as a guide groove provided in the mount 361, in order to ensure the orientation of the luminophore unit 365 in its mount 362. Such guide crosspieces 375 and guide grooves 362 are illustrated in FIG. 16 or 12.

Thus, a combined use of luminophores and biosensors will be made possible overall, whereby a luminophore unit 365 and a biosensor unit 355 are integrated into a housing 305. Luminophores can thereby be introduced individually into the cavities 382. Such a multi-sensor component makes it possible to combine in one port the parameters optimal for process control in a selected measurement range, parameters such as pH, $pO_2$, $pCO_2$, temperature, concentration of saccharides, proteins, ions, impedance for cell growth, etc., whereas a use only of luminophores in one port (or only a use of biosensors in one port) would not makes possible a process control of all of these parameters.

What is claimed is:

1. A multi-sensor component for the installation sensors at an individual port of a container for culturing biological material, the component comprising:
   a housing having a front housing segment, the front housing segment being capable of being introduced into an uptake opening of the individual port so that the front housing segment faces the container;
   a first mount for a first sensor unit arranged in the front housing segment; and
   a second mount for a second sensor unit arranged in the front housing segment, wherein the first and second sensor units are configured to simultaneously determine different parameters from one another and/or different analytes from one another.

2. The component of claim 1, further comprising the first sensor unit secured to the first mount and/or the second sensor unit secured to the second mount.

3. The component of claim 2, wherein the first and/or second sensor unit is a biosensor unit.

4. The component of claim 3, wherein the biosensor unit is a flat chip.

5. The component of claim 2, wherein one of the first and second sensor units is a luminophore unit for luminescence-based parameter measurement.

6. The component of claim 5, wherein the luminophore unit comprises a basic body with a cavity accommodating a luminophore substance.

7. The component of claim 6, wherein the basic body comprises a front region and a back region, the front region facing the container and the back region facing an outside of the container, wherein the front region comprises the cavity, and wherein the back region comprises a light source and/or a photoelement.

8. The component of claim 6, wherein the luminophore substance comprises a material selected from a group consisting of: graphene quantum dots, (GQDs), heterocyclic GQDs (e.g. N-GQDs), an organometallic compound, ground glass powder, and xerogel.

9. The component of claim 7, wherein the front region comprises glass or glass ceramics.

10. The component of claim 9, wherein the back region comprises optical fibers forming a light guide.

11. The component of claim 10, wherein the front region has a disc shape and the back region has a rod shape, and wherein the basic body further comprises a laser weld securing the front and back regions to one another.

12. A biological material culturing container, comprising:
   a container with an inside and an outside;
   a port that connects the inside to the outside;

a sensor uptake having an inner uptake opening, wherein the sensor uptake has a front sensor uptake section in the port so that the inner uptake opening extends through the port;

a multi-sensor component having a housing with a front housing segment, the front housing segment being introduced into the inner uptake opening so that the front housing segment faces the container;

a first mount for a first sensor unit arranged in the front housing segment; and a second mount for a second sensor unit arranged in the front housing segment, wherein the first sensor unit is secured to the first mount and/or the second sensor unit is secured to the second mount, and wherein the first sensor unit is a biosensor unit and the second sensor unit is a luminophore unit for luminescence-based parameter measurement.

13. The container of claim 12, wherein the luminophore unit comprises a basic body with a cavity accommodating a luminophore substance, a front region, and a back region, the front region facing the container and the back region facing an outside of the container, wherein the front region comprises the cavity, and wherein the back region comprises a light source and/or a photoelement.

14. The container of claim 13, wherein the luminophore substance comprises a material selected from a group consisting of: graphene quantum dots, (GQDs), heterocyclic GQDs (e.g. N-GQDs), an organometallic compound, ground glass powder, and xerogel.

15. The container of claim 13, wherein the front region comprises glass or glass ceramics and the back region comprises optical fibers forming a light guide.

16. The container of claim 15, wherein the front region has a disc shape and the back region has a rod shape, and wherein the basic body further comprises a laser weld securing the front and back regions to one another.

17. A method for producing a multi-sensor component, comprising:

providing a luminophore sensor unit;

providing a housing comprising polyether ether ketone (PEEK) that can be introduced at least by a front housing segment into an uptake opening extending through a port of a container so that the front housing segment is facing the inside of the container;

providing the housing with a recess for the luminophore sensor unit bringing about a relative expansion of the housing with respect to the luminophore sensor unit by heating the housing;

inserting the luminophore sensor unit into the recess of the housing while expanded;

bringing about a relative contraction of the housing with respect to the luminophore sensor unit by cooling the housing so that the housing solidly accommodates the luminophore sensor unit in the recess.

* * * * *